United States Patent [19]

Van Arsdell

[11] Patent Number: 4,947,348
[45] Date of Patent: Aug. 7, 1990

[54] DENSITOMETER METHOD AND SYSTEM FOR IDENTIFYING AND ANALYZING PRINTED TARGETS

[75] Inventor: Robert D. Van Arsdell, Wappingers Falls, N.Y.

[73] Assignee: Kollmorgen Corporation, Simsbury, Conn.

[21] Appl. No.: 30,735

[22] Filed: Mar. 25, 1987

[51] Int. Cl.⁵ .............................................. G06F 9/00
[52] U.S. Cl. .................................... 364/523; 364/518; 101/181
[58] Field of Search ............... 364/523, 522, 521, 518; 101/171, 211, 181, 248; 358/75, 80

[56] References Cited

U.S. PATENT DOCUMENTS

| | | | |
|---|---|---|---|
| 3,933,094 | 1/1976 | Murphy et al. | 101/426 |
| 3,970,394 | 7/1976 | Stanton | 356/195 |
| 4,239,393 | 12/1980 | Tobias | 356/407 |
| 4,544,271 | 10/1985 | Yamamoto | 356/328 |
| 4,546,700 | 10/1985 | Kishner et al. | 101/211 |
| 4,706,206 | 11/1987 | Benoit et al. | 364/526 |
| 4,717,954 | 1/1988 | Fujita et al. | 358/80 |

FOREIGN PATENT DOCUMENTS 3220378  12/1983  Fed. Rep. of Germany .

OTHER PUBLICATIONS

Macbeth brochure entitled "A Quality Control Station in One Hand . . . Anywhere . . . Anytime: Macbeth RD-505 Portable Reflection Densitometer".
Macbeth brochure entitled "The On-Press Color Monitor by Macbeth".
Macbeth brochure entitled "Macbeth Introduces Non-Stop Color Control".
Macbeth brochure entitled "Macbeth Press Control System with Automatic Ink Control".
Macbeth brochure entitled "Waste, Profit and the Macbeth Press Control System".

Primary Examiner—Gary V. Harkcom
Assistant Examiner—Phu K. Nguyen
Attorney, Agent, or Firm—Morgan & Finnegan

[57] ABSTRACT

A hand-held battery operated densitometer for identifying and analyzing printed targets is provided which automatically determines whether an unprinted substrate, a solid black, a muddy magenta solid, an overprint, a solid color, or a halftone has been detected. Referenced density values measured through red, green, blue and visual optical filters for an overprint and the first and second down colors are used to determine and display percent trap. Referenced density values for halftone and corresponding solid targets are used to determine and display percent dot area. Referenced density values for solid targets may also be displayed. The printing process is adjusted based upon the displayed solid densities, percent trap and percent dot area.

18 Claims, 4 Drawing Sheets

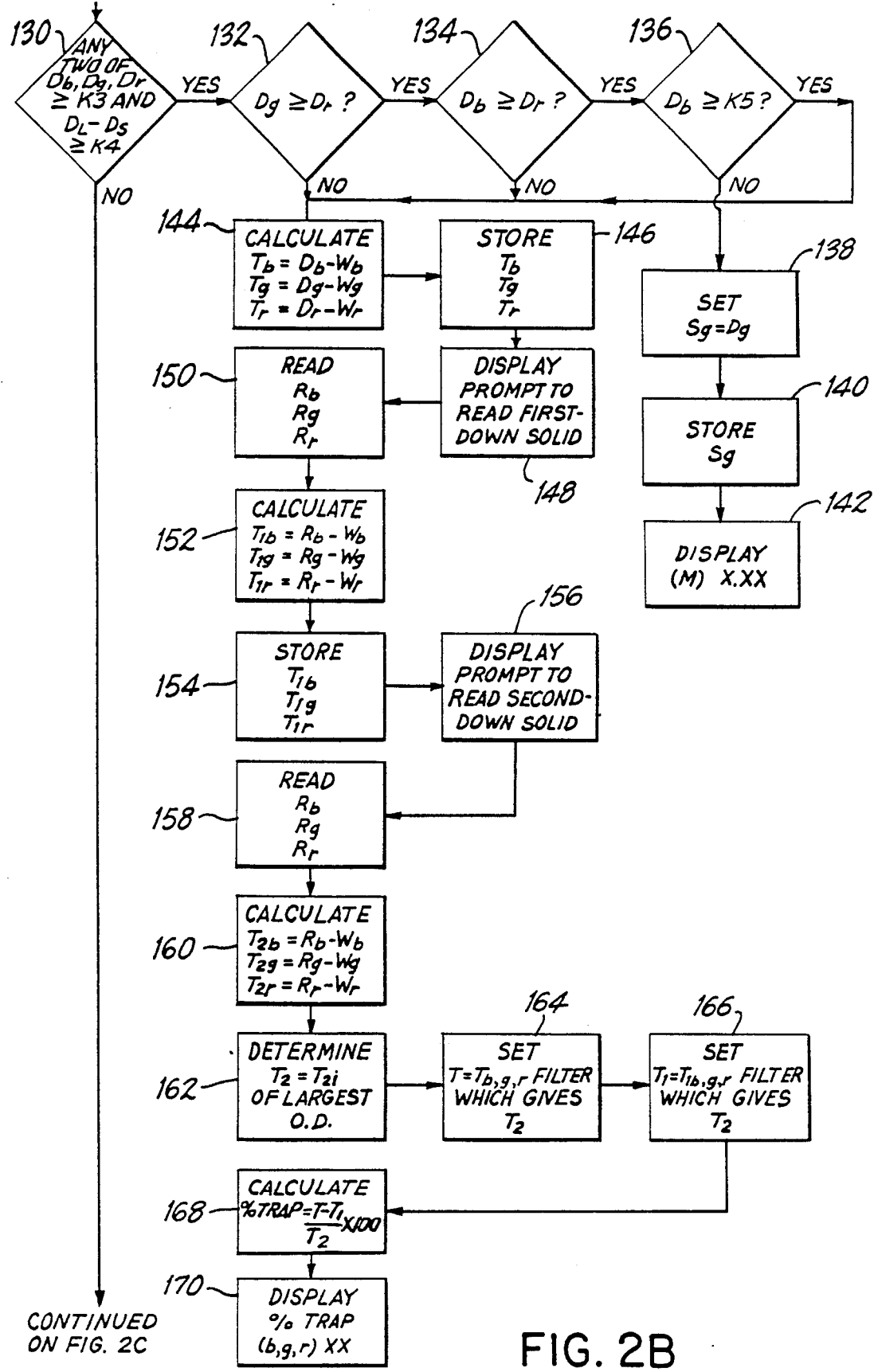

DENSITOMETER METHOD AND SYSTEM FOR IDENTIFYING AND ANALYZING PRINTED TARGETS

TECHNICAL FIELD

The present invention relates to a densitometer method and system and, more particularly, to a densitometer useful for printing process control.

BACKGROUND AND OBJECTS OF THE INVENTION

An optical densitometer is a device used to determine the optical density of printed ink films. A densitometer normally contains four optical filters each matched to one of the four standard printing ink colors, cyan, magenta, yellow and black.

The densitometer is an indispensable tool to the pressmen who operate four color lithographic presses. It provides accurate, repeatable and objective readings of optical density of solid patches of ink, halftone patches and overprinted patches. Density readings taken on these patches are used to adjust inking levels on the press and to adjust other printing parameters such as dampening solution levels and roller nip pressures.

The densitometer user normally performs a referencing procedure before measuring the density of printed ink. The optical density of a patch of the unprinted substrate is read through each of the four filters. These densities are designated as reference densities by the user and stored as such in the densitometer's memory. If the readings are made but not designated as reference readings, they will not be stored as such and the user will subsequently read densities erroneously believed to be referenced to the unprinted substrate. Actual density readings require the user to first identify the color of the target patch and decide whether the target is a solid, halftone or overprinted patch. The user must also correctly match the target patch color to the filter chosen to read the optical density. An error at any point in this procedure will, of course, yield a useless density reading since it is misidentified. By way of example, it is possible to confuse cyan and blue or red and magenta.

While taking readings during a press run, the pressman must concentrate on performing the correct sequence of events. He is necessarily distracted from the more important business of monitoring the behavior of the press. Also, if the densitometer is not easily portable, the pressman's movement is restricted by the length of the densitometer's line cord. A densitometer that cannot be held in one hand when operated is less convenient to use than a hand-held version of the same device.

It is desirable to eliminate user error to the extent possible, since user error results in wasted printing material and lost time. Thus, it would be highly desirable to provide a densitometer capable of automatically performing decision-making tasks. Such tasks include (i) the ability to recognize unprinted substrate and read and store all four filter position densities as reference densities, (ii) the ability to identify the color of the target being read, match the color to the appropriate filter and display the appropriate density, (iii) the ability to distinguish among a group of solid patches, (iv) the ability to distinguish between solids and halftones, solids and overprints and halftones and overprints, (v) the ability to determine and display percent trap of an overprint and (vi) the ability to determine and display percent dot area of a halftone.

A densitometer capable of performing the above mentioned decision-making tasks in an unaided manner would advantageously reduce user error and free the pressman to concentrate on operating the press rather than the densitometer. A battery operated, hand-held densitometer which is capable of performing the above tasks would be even more desirable since it could be taken anywhere in the pressroom area to read optical density.

Gretag introduced a hand-held battery operated densitometer, the Gretag D-1, in 1966. This densitometer does not read all four filter positions automatically for each sample and does not perform the decision-making tasks described above.

Macbeth® introduced the TDA-1000 densitometer in 1970. This device provided four sequential readings of each sample. It was not a portable device, however, and did not perform decision making tasks. In 1977, Macbeth® introduced the On-Press Color Monitor, an on-line densitometer which took four simultaneous readings of optical density on four successively positioned color patches. The color and relative position of each patch was preprogrammed into the memory of the on-line operating system. The densitometer consisted of four distinct sets of light sources and filtered detectors. This device was not portable and did not perform the type of decision-making tasks described above. In 1981, Macbeth® introduced a version of the On-Press Color Monitor using a single light source and a fiber optic probe which was a single bundle at the point where light reflected from the sample was collected and which was then separated into four bundles (quadrifurcated). Each of these bundles passed a portion of the reflected light through a blue, green, red or visual filter, respectively, to one of the four detectors. This device was not portable and could not perform the types of decision-making tasks described above.

U.S. Pat. No. 4,239,393 issued to Tobias in 1980 describes a densitometer containing a rotating filter wheel having red, green and blue filters which make it possible to read three densities automatically for each sample. This device is not portable, does not provide a separate filter matched to black ink, and is not capable of performing decision-making tasks.

In 1986, X-Rite introduced the X-Rite 408 Color Reflection Densitometer. This device is battery operated and hand-held. It uses a rotating filter wheel to read all four filter positions for each sample. It displays the largest optical density reading of the four filters. This device does not distinguish between solids and halftones, solids and overprints or overprints and solids. Nor does it recognize an unprinted substrate as a reference without operator instruction.

Therefore, it is an object of the present invention to provide a portable hand-held densitometer.

Another object of the present invention is to provide a densitometer which automatically recognizes unprinted substrate, overprints, solids and halftones.

Another object of the present invention is to provide a densitometer which automatically selects and displays appropriate density measurements.

A further object of the present invention is to provide a densitometer which automatically selects the appropriate density measurements and calculates and displays the percent trap of an overprint.

Yet a further object of the present invention is to provide a densitometer which automatically selects the appropriate density measurements and calculates and displays percent dot area.

These and other highly desirable and remarkable results are accomplished by the present invention in a portable, hand-held densitometer which automatically determines type of the target being measured, stores pertinent measured parameters therefrom and, where appropriate, determines and displays vital information parameters such as percent trap and percent dot area for use by the pressman in adjusting and controlling the printing press.

Objects and advantages of the invention are set forth in part herein and in part will be obvious herefrom, or may be learned by practice with the invention, the same being realized and attained by means of the instrumentalities and combinations pointed out in the appended claims.

The invention consists in the novel parts, constructions, arrangements, combinations, steps and improvements herein shown and described.

SUMMARY OF THE INVENTION

In accordance with the present invention a densitometer method and system are provided which automatically recognize the type of target measured, updates appropriate memory registers with information from the particular target measured and, where appropriate, determines percent trap in an overprint and percent dot area in a halftone. Appropriate density, color, percent trap and percent dot area information is displayed to the pressman, for use in controlling the printing process.

The densitometer according to the present invention includes a convenient measuring head which illuminates a sample target with annular illumination and collects the reflected light in a fiber optic bundle. The reflected light is transmitted to the densitometer body through the fiber optic bundle, where the bundle is divided into four separate bundles, i.e., quadrifurcated, each bundle being associated with a dedicated optical filter and detector. The filters used are red, green, blue and visual optical filters. The filtered light is detected by the dedicated detectors and the analog signals from all four detectors are multiplexed, converted to digital signals by an analog to digital converter, and sent to a microprocessor for analysis. Analyzed data from the microprocessor is displayed to the pressman for use in controlling the printing process.

The digital data is analyzed by the microprocessor in order to determine whether an unprinted substrate, a solid black, a muddy magenta solid, an overprint, a solid color or a halftone has been detected.

Unprinted substrate is identified by comparing referenced optical densities, i.e. measured optical densities minus corresponding stored substrate optical densities, if any, to a first stored constant K1 and, where available, to stored substrate optical density values. Where all referenced optical densities values are less than K1 or the stored substrate density values it is assumed that an unprinted substrate has been measured, the substrate density values in memory are updated with unreferenced measured optical densities, and the fact that an unprinted substrate has been referenced is displayed to the pressman. The pressman then moves the measuring head to a different target.

Where an unprinted substrate is not detected, the referenced densities $D_r$, $D_g$, $D_b$ are compared to a second stored constant K2. If all values of $D_r$, $D_g$, $D_b$ are greater than or equal to K2 it is assumed that a solid black target has been detected, the referenced visual density reading $D_v$ is stored in memory as the corresponding solid density $S_v$, and the fact that a solid black patch has been read is displayed to the pressman, who then moves the measuring head to a different target.

Where neither an unprinted substrate nor a solid black is detected, a determination is made whether an overprint has been detected. In order to make this decision the densitometer determines whether any two of $D_r$, $D_g$, $D_r$ are greater than or equal to a third stored constant K3 and whether the difference between the largest and smallest referenced density values is greater than or equal to a fourth stored constant K4. If any two of the densities are greater than or equal to K3 and the difference is greater than or equal to K4, then a determination must be made whether an overprint or a "muddy magenta" solid has been detected. This determination is made by comparing $D_g$ to $D_r$, $D_b$ to $D_r$ and/or $D_b$ to a fifth stored constant K5. If a muddy magenta has been detected the green density $D_g$ is stored as the green solid density $S_g$ and the density of the muddy magenta patch is displayed to the pressman, who then moves the measuring head to a different target. If, however, an overprint is detected, the densitometer prompts the pressman to provide readings from a sample of the first and second down colors and then calculates and displays percent trap to the pressman, who thereafter moves the measuring head to a different target. Percent trap is a measure of the ability of the first down color to serve as a substrate for the second down color.

Where none of an unprinted substrate, a solid black, muddy magenta or an overprint are detected, the densitometer determines whether a solid color patch of cyan, magenta or yellow has been read by determining whether any of $D_r$, $D_g$ $D_b$ are greater than or equal to sixth stored constant K6. If so, the densitometer assumes it has detected a solid patch corresponding to the filter which provided the largest referenced density measurement, stores the largest measured density as the corresponding solid density, and displays the solid density and, optionally, color to the pressman. The pressman then moves the measuring head to a different target.

Where no unprinted substrate, solid black, muddy magenta solid, overprint or color solid is detected, the densitometer assumes it has detected a halftone target. The densitometer then determines whether a black halftone has been detected by comparing the difference between the largest and smallest referenced density readings to a seventh stored constant K7. If a black halftone is indicated the densitometer memory is check for a stored value of the corresponding black solid density, $S_v$. If the stored value of $S_v$ is greater than the second stored constant K2 the visual density reading $D_v$ is stored as $D_h$ and the percent dot area is calculated using $D_h$ and S in the Yule-Nielsen equation. The percent dot area is displayed to the pressman, who thereafter moves the measuring head to a different target. If the halftone is not black, however, the largest measured density is stored as $D_h$ and the densitometer checks to determine whether the corresponding solid density S for that color has been stored. If the corresponding stored S value is greater than or equal to the sixth stored constant K6 percent dot area for the halftone is determined using $D_h$ and the corresponding solid color density S in the Yule-Nielsen equation. The percent dot area and, optionally, color are displayed to the pressman and another target may then be measured. However, where the black solid density $S_y$ is less than K2, where the appropriate color solid density is less than K6 or where the appropriate S value has not been measured and stored the densitometer displays an error code indicating to the pressman that no usable solid target has been measured and, consequently, percent dot area cannot be calculated.

Based upon the various information displays the pressman adjusts the printing process to maintain print quality.

It will be readily appreciated that the densitometer according to the present invention can be provided in a hand-held, battery-operated portable unit which may be conveniently carried to various points in the pressroom. It will also be appreciated that the densitometer system and method according to the present invention, by automatically distinguishing among various solid and halftone and color and black targets, substantially reduces operator error resulting from misidentified targets and use of improper values for calculations of percent trap and percent dot area.

Advantageously, all of the intelligent determinations made by the densitometer using the system and method of the present invention free the pressman from having to make similar determinations based upon his experienced observations. Thus, the present densitometer system and method remarkably enable the pressman to devote his attention primarily to operating the press and adjusting the printing process rather than to using his valuable experience and knowledge to recognize print targets and ensure that properly referenced measurements from appropriate targets are used to determine percent trap and percent dot area.

It will be understood that the foregoing general description and the following detailed description as well are exemplary and explanatory of the invention but are not restrictive thereof.

BRIEF DESCRIPTION OF THE DRAWINGS

The accompanying drawings, referred to herein and constituting a part hereof, illustrate preferred embodiments of the system and method of the present invention, and together with the description serve to explain the principles of the invention, in which:

FIGS. 2A, 2B and 2C are a flow chart diagram of the method of analysis according to the invention used in the densitometer system to determine the type of target being viewed and to determine and display appropriate process information used in controlling the printing process.

DETAILED DESCRIPTION OF THE PREFERRED EMBODIMENTS

Figure 1:
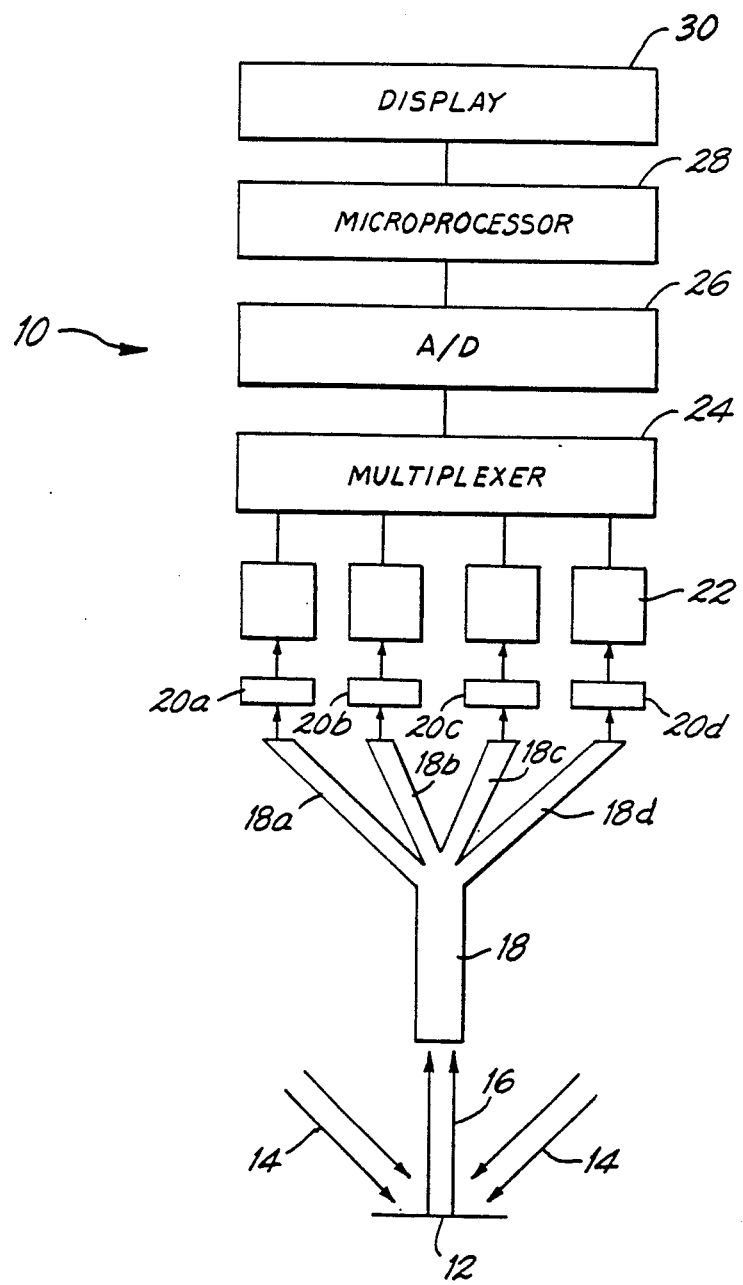
FIG. 1 is a partial schematic diagram of the densitometer system of the present invention.

Referring more particularly to FIG. 1, there is shown a densitometer system 10 in accordance with the present invention. As shown, a sample 12 is annularly illuminated by light rays 14 and reflected light rays 16 are collected by one end of a fiber optic bundle 18. Preferably, the sample is illuminated at a 45° angle and the reflected light rays are collected at 0° to the sample normal as shown. The other end of the fiber optic bundle is quadrifurcated so that the reflected light is divided among four separate bundles 18a, 18b, 18c, 18d and directed through red, green, blue and visual optical filters 20a, 20b, 20c, 20d, respectively, to a set of detectors 22. Analog signals from each of the detectors are sent to a multiplexer 24 which sequentially passes the analog signals to an analog to digital signal converter 26. The digital signals are then sent to a microprocessor 28 which is programmed to analyze to digital signals so as to determine what has been detected and what pertinent information should be displayed on display 30 to the pressman so that appropriate process control adjustments may be made based upon the displayed information. Advantageously, the entire densitometer system may be provided in a hand-held, battery-operated unit with a convenient measuring probe head attached to the densitometer system via the fiber optic bundle.

The logic system utilized in the present invention makes use of the fact that the lithographic printing process is a subtractive color system. That is, the printing inks commonly used are chosen for their ability to selectively absorb rather than reflect particular colors. Thus, the three colored inks cyan, magenta and yellow absorb red, green and blue light, respectively. Consequently, a red optical filter passes a relatively small fraction of light reflected from a cyan ink patch, a green filter passes a relatively small fraction of light reflected from a magenta ink patch, and a blue filter passes a relatively small fraction of light reflected from a yellow ink patch. In order for the subtractive color system as a whole to be effective, however, it is necessary that the printing inks be "transparent", that is, able to pass, unscattered, the light wavelengths not absorbed. It is therefore clear that an overprint of cyan and magenta inks reflects essentially only blue light. Likewise, an overprint of cyan and yellow inks reflects essentially only green light, and an overprint of magenta and yellow inks reflects only red light. Black ink is also used in lithographic printing to add contrast and darken printed images. Black ink is much more neutral than cyan, magenta or yellow ink in that it absorbs light more uniformly across the visible spectrum. For detection purposes, an optical filter for black ink is one which mimics the sensitivity of the normal human eye across the spectrum of visible light. Such a filter is simply called a "visual" filter. In printing, the absorbance of each ink and, hence, the final image created by the combined absorbance of all inks, is primarily controlled by varying the fraction of the image area on a printing plate that is receptive to ink rather than by varying the thickness of the ink film. This ink receptivity is controlled by using ink sensitive dots of various sizes on the printing plate. All partially sensitized image areas of a printing plate are called "halftones" although the sensitized fractions do not always comprise half the total plate area.

It has been found that cyan, magenta and yellow ink films are inter-distinguishable since each film provides a relatively high absorbance when read through a particular filter. Black ink is distinguishable from the color inks due to its neutral optical behavior. In addition, solid ink films of a single ink are distinguishable from halftones of the same color by the relatively low overall density of the halftones. Overprints are distinguishable from single layer ink films by the fact that overprints provide two relatively high absorbance readings instead of one, as with single ink films. Finally, an unprinted substrate is distinguished by the very low density read through all filters.

The following definitions will be useful in understanding the logic system of the densitometer according to the invention.

O.D. = optical density
r = red filter reading
g = green filter reading
b = blue filter reading
v = visual filter reading
W = unprinted substrate or "white" O.D., i.e. $W_r$ is the unprinted substrate O.D. read through a red filter.
R = unreferenced target O.D.
D = referenced O.D. reading of a given target, i.e. R - W.
S = referenced solid O.D., i.e. R - W for a solid reading.
T = referenced trap or overprint O.D., i.e. R - W for an overprint.
$T_1$ = referenced solid O.D. corresponding to the first-down ink in a given overprint, i.e. R - W for a given solid.
$T_2$ = referenced solid O.D. corresponding to the second-down ink in a given overprint, i.e. R - W for a given solid.
K1 = upper O.D. limit for D of unprinted substrate (typically 0.1 O.D.).
K2 = lower O.D. limit for $D_b$, $D_g$, $D_r$, $D_v$ of a black solid (typically 1.0 O.D.).
K3 = lower O.D. limit for D of each of the largest two O.D. readings of an overprint (typically 0.8 O.D.).
K4 = lower limit of O.D. difference between D's of largest O.D. filter reading and smallest O.D. filter reading of black halftone (typically 0.3 O.D.).
K5 = lower O.D. limit for $D_b$ of a red overprint (typically 1.0 0.D).
K6 = lower O.D. limit for D of solid patches read through the filter of largest O.D. (typically 1.0 O.D. for cyan, magenta and black inks and 0.8 O.D. for yellow ink).
K7 = upper limit of O.D. difference between D's of largest O.D. filter reading and smallest O.D. filter reading of black halftone (typically 0.05 O.D.).

Using the above definitions, the logic system and method according to the present invention can be described as follows with reference to the flow chart shown in FIGS. 2A, 2B and 2C.

The densitometer reading head is engaged and the densitometer determines whether there are W values in memory for the unprinted substrate optical densities. See FIG. 2A, steps 100, 102, respectively.

If there are no W values in memory all W values are set equal to 0 (FIG. 2A, 104) and the unreferenced optical densities $R_r$, $R_g$, $R_b$, $R_v$ of the unprinted substrate are stored as $W_r$, $W_g$, $W_b$, $W_v$, respectively. FIG. 2A, 106. The measured density readings are then converted to referenced density values by subtracting the newly or previously stored W values from the unreferenced density readings. For example, the referenced red density $D_r = R_r - W_r$. FIG. 2A, 108, 110.

Figure 2A:
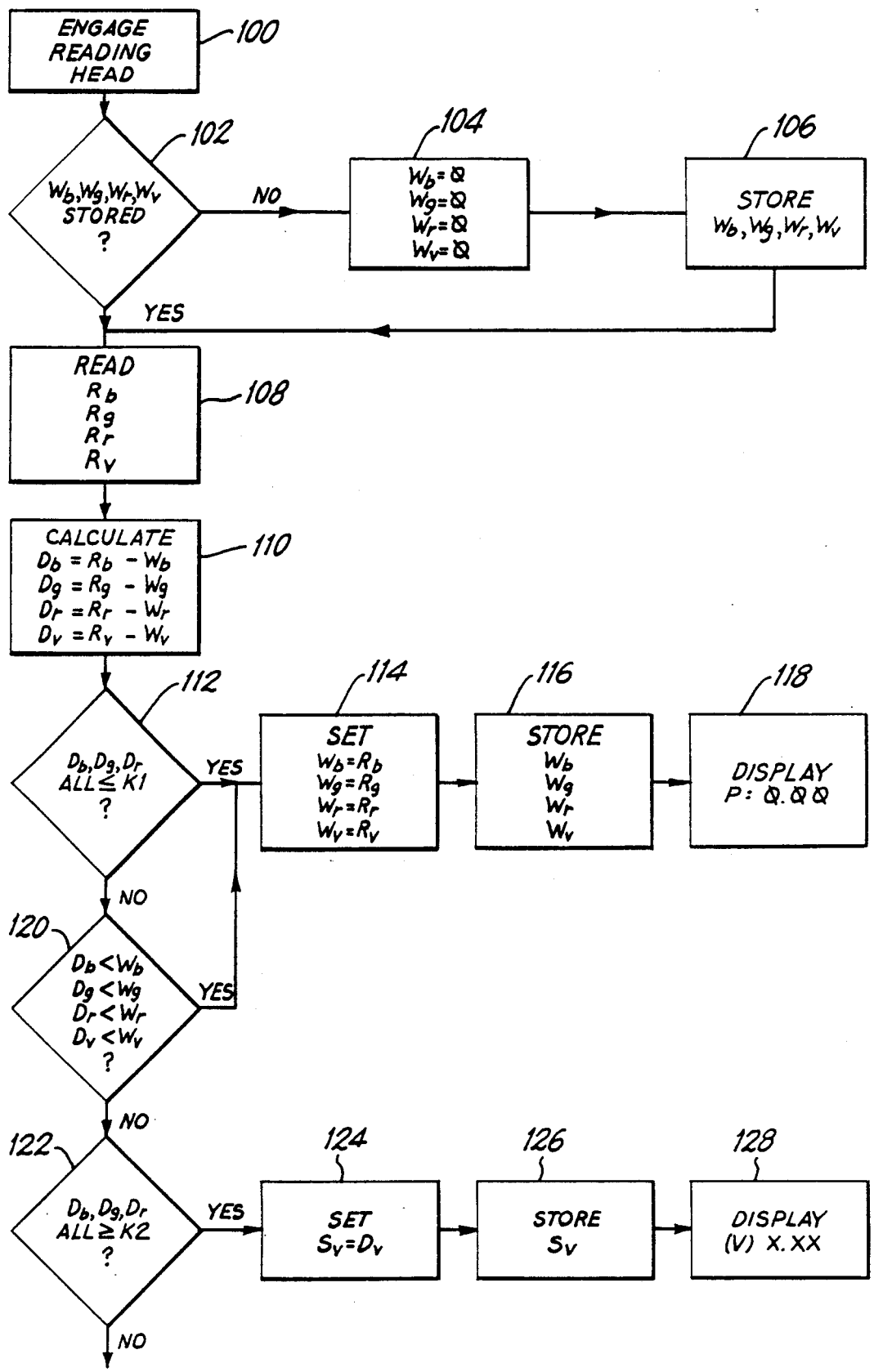

If $D_r$, $D_g$, $D_b$ are all less than stored constant K1 (FIG. 2A, 112) or if all D values are less than corresponding stored W values (FIG. 2A, 120) then it is assumed that unprinted substrate has been read and the W values in memory are updated with unreferenced optical density R values. That is, each W memory is set as follows: $W_r = R_r$, $W_g = R_g$, $W_b = R_b$, $W_v = R_v$ (FIG. 2A, 114, 116). At this point, "P.0.00" is displayed to the pressman to indicate that unprinted substrate, usually paper, has been read and that a reference reading has been taken. (FIG. 2A, 118). At this point the pressman moves the measuring head to another target. If, however, $D_r$, $D_g$, $D_b$ are not all less than stored constant K1, (FIG. 2A, 112) and all of $D_r$, $D_g$, $D_b$, $D_v$ are not less than the corresponding W values (FIG. 2A, 120), then it is assumed that unprinted substrate has not been detected and the next step of analysis is executed.

Where unprinted substrate is not detected, the densitometer next determines whether $D_r$, $D_g$, $D_b$ are all greater than or equal to stored constant K2 (FIG. 2A, 122). If so, it is assumed that a solid black target has been read and $D_v$ is stored as $S_v$ (FIG. 2A, 124, 126) for later use in the calculation of dot area when a black halftone target is read. $D_v$ and, optionally, the black color of the target are displayed to the pressman (FIG. 2A, 128), who then moves the portable measuring head to a different target location. If, however, $D_r$, $D_g$, $D_b$ are not all greater than or equal to K2, then it is assumed that the target measured is not a solid black ink film and the next step of analysis is performed.

Where neither an unprinted substrate nor a solid black target is detected, a check for an overprint is made. See FIG. 2B. If any two of $D_r$, $D_g$, $D_b$ are greater than or equal to stored constant K3 and if the difference between the largest and smallest densities (shown in FIG. 2B as $D_L - D_s$) is greater than or equal to stored constant K4 (FIG. 2B, 130), then the following overprint check is performed. If $D_g$ is less than $D_r$ (FIG. 2B, 132) then a green overprint is assumed. If, however, $D_g$ is greater than or equal to $D_r$ then a check is made of $D_b$ against $D_r$. If $D_b$ is less than $D_r$ then a blue overprint is assumed (FIG. 2B, 134), whereas if $D_b$ is greater than or equal to $D_r$, then $D_b$ is checked against stored constant K5 (FIG. 2B, 136). If $D_b$ is less than K5 then it is assumed that a "muddy magenta" solid has been read rather than an overprint. A muddy magenta is a magenta wherein $D_b$ and $D_r$ are relatively high with respect to $D_g$. If a muddy magenta solid has been detected, $D_g$ is stored as $S_g$ (FIG. 2B, 138, 140) for later use in the calculation of dot area. $D_g$ and, optionally, the color of the target are displayed to the pressman (FIG. 2B, 142), who then moves the densitometer measuring probe head to measure a different target. If, on the other hand, $D_b$ is greater than or equal to K5 (FIG. 2B, 136) it is assumed that a red overprint has been detected.

Where it is assumed that an overprint has been read, $D_r$, $D_g$, $D_b$ are stored as overprint density values $T_r$, $T_g$, $T_b$ (FIG. 2B, 144, 146), respectively. The densitometer then prompts the user, by displaying a predetermined code or other indicator, to provide a reading of a solid patch of the first-down color of the overprint (FIG. 2B, 148). The measured values $R_r$, $R_g$, $R_b$ for the first down color are converted to referenced density values by subtracting the corresponding unprinted substrate densities and are respectively stored as $T_{1r}$, $T_{1g}$, $T_{1b}$ (See FIG. 2B, 150, 152, 154). The densitometer then prompts the user for a reading of a solid patch of the second-down overprint color (FIG. 2B, 156). The unreferenced second-down color density readings are converted to referenced densities $T_{2r}$, $T_{2g}$, $T_{2b}$ (FIG. 2B, 158, 160), respectively. The largest density reading of the second-down color selected from among $T_{2r}$, $T_{2g}$, $T_{2b}$ is stored as $T_2$ (FIG. 2B, 162). The filter color designated as $T_2$ is then used to designate the corresponding T and $T_1$ (FIG. 2B, 164, 166). For example, if the largest second-down color reading is $T_{2r}$, $T_{2r}$ is designated $T_2$ and $T = T_r$ and $T_1 = T_{1r}$. The densitometer system then calculates percent trap, an expression of the ability of the first-down ink in an overprint to serve as a printing substrate for the second-down color, using equation (1).

$$\text{Percent Trap} = \frac{T - T_1}{T_2} \times 100 \quad (1)$$

Figure 2C:
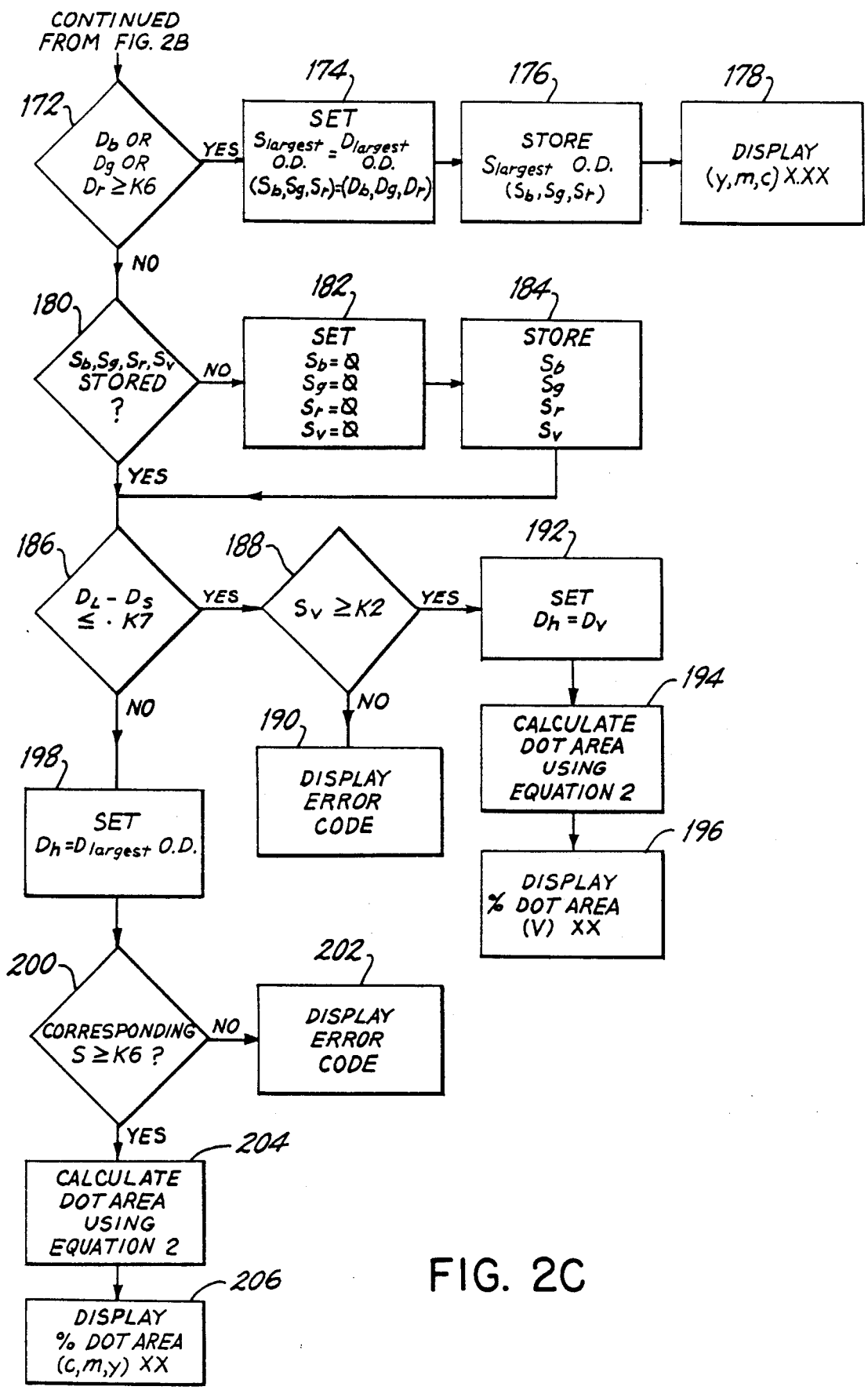

Ideally, of course, $T = T_1 + T_2$ and the percent trap is 100%. The calculated percent trap is displayed to the pressman for use in controlling the printing process (See FIG. 2B, 168, 170), whereafter the pressman moves the measuring probe to another target. It is also contemplated that the color of the overprint, i.e. red, green or blue, could be displayed to the pressman as well.

Where unprinted substrate, a black solid, a muddy magenta solid or an overprint is not detected, then each of $D_r$, $D_g$, $D_b$ is checked against stored constant K6 (FIG. 2C, 172). If any one of $D_r$, $D_g$, $D_b$ is greater than or equal to K6, then it is assumed that a color solid target has been read. The color of the target is assumed to be the color associated with the filter reading that yields the largest density value. Therefore, the largest density value among $D_r$, $D_g$, $D_b$ is assigned to a corresponding memory value $S_r$, $S_g$, $S_b$ and stored for later use in calculating dot area (FIG. 2C, 174, 176). The density value and, optionally, the color of the target are displayed to the pressman (FIG. 2C, 178), who then moves the densitometer probe head to measure a different target.

Where none of an unprinted substrate, a solid black, a muddy magenta, or a color solid has been detected, it is assumed that a halftone target has been measured and the densitometer checks for stored solid density values $S_r$, $S_g$, $S_b$, $S_y$ (FIG. 2, 180). Where no S values exist, $S_r$, $S_g$, $S_b$ and $S_y$ are set equal to 0 (FIG. 2C, 182, 184).

The densitometer then determines whether the difference between the largest and smallest measured densities (shown in FIG. 2C as $D_L$-$D_s$) is less than or equal to stored constant K7 (FIG. 2C, 186). If so, the measured target is assumed to be a black halftone and the stored value of $S_y$ is checked to determine whether percent dot area can be calculated (FIG. 2C, 188). If $S_y$ is less than K2, no calculation of percent dot area can be made and an error signal is displayed to the pressman (FIG. 2C, 190) indicating that no usable solid black target has been measured for use in calculating dot area. However, if $S_y$ is greater than or equal to K2, then $D_h$ is set equal to referenced density $D_y$ (FIG. 2C, 192) and the dot area is calculated (FIG. 2, 194) by use of the Yule-Nielsen equation (2).

$$\text{Percent dot area} = \frac{1 - 10^{-D_h/n}}{1 - 10^{-S/n}} \times 100 \quad (2)$$

where:
$D_h$ = the largest measured density value D for the halftone
S = the corresponding solid density
n = Yule-Nielsen correction factor for paper scattering The calculated percent dot area is displayed to the pressman (FIG. 2C, 196). In this case, where the halftone is assumed to be black $D_h = D_y$ and $S = S_y$, both read through the visual filter. The pressman uses the percent dot area data to control the printing process and moves the densitometer head to a different target location.

Where the difference between the largest and smallest density values is greater than stored constant K7 (FIG. 2C, 186), then it is assumed that the target measured is a cyan, magenta or yellow halftone patch. It is assumed that the color of the ink patch corresponds to the largest referenced density value measured through one of the red, green or blue optical filters, so the largest referenced density is stored as $D_h$ (FIG. 2C, 198). If the solid density S corresponding to the largest measured density, i.e. $D_h$, is less than stored constant K6 (FIG. 2C, 200), then no usable solid patch has been read and an error message is displayed to the pressman (FIG. 2C, 202) indicating that no usable corresponding solid patch has been read. If, on the other hand, the solid density S corresponding to the largest measured density is greater than or equal to K6, then percent dot area for the color halftone patch is calculated using equation (2), above, and displayed to the pressman (See FIG. 2C, 204, 206). Of course, it is contemplated that halftone color could also be displayed.

All of the stored constant values referred to herein are set based upon experience with the properties of the particular type of target involved. The typical values set forth above in defining each constant are based upon the inventors' experience with the invention and are intended to provide working knowledge as to how the constant may be set in order to make use of the invention. Of course it is contemplated that variation of the constants may be desirable depending upon the particular paper and the types and combinations of inks used in a given process.

Although the foregoing discussion has been directed to use of referenced density measurements, it is contemplated that unreferenced density measurements could be used, albeit less satisfactorily, with the present system. In addition, the foregoing discussion is merely intended to set forth the preferred logic system for the step by step analysis of measured data to determine what type of target has been measured and, where appropriate, percent trap or percent dot area and to display density, percent trap or percent dot area to the pressman for use in controlling the printing process. It is contemplated, of course, that it may be possible to develop variations of the particular logic sequence herein described and shown which are capable of making the necessary determinations to accomplish the automatic densitometer in accordance with the invention.

In use, the pressman carries the hand-held, battery operated densitometer to any particular measuring location in the pressroom. The measuring probe head is placed against a printed target or unprinted substrate and a reading is taken. The densitometer automatically indicates the density and, optionally, color of the target measured. The pressman consecutively positions the measuring head on a number of targets, with the densitometer displaying density and perhaps color after each measurement and storing appropriate density information for later use in calculating percent trap and percent dot area. Where necessary, the densitometer prompts the pressman to provide measurements of the first and second down colors of an overprint so that percent trap can be calculated or indicates that an appropriate solid density reading is necessary before percent dot area can be calculated. Based upon the information displayed the pressman can determine what adjustments to the printing process, if any, are necessary and can provide measurements of particular targets indicated to be necessary by the densitometer.

Since the densitometer automatically determines what target has been read, stores appropriate density information and calculates and displays percent trap and percent dot area, all in a portable hand-held device, the pressman can devote his attention and experience primarily to adjusting the press and printing process rather than to recognizing targets, selecting and storing appropriate density values, ensuring that those selected values are properly referenced, and calculating percent trap and percent dot area.

Thus, the densitometer method and system according to the present invention advantageously permit accurate, reliable and convenient measurement of a variety of printed targets in a heretofore unknown fashion. Remarkably, all measuring electronics and display can be mounted in a relatively small and lightweight battery-operated densitometer body having a versatile measuring head connected to the densitometer by an electro-optic cable. In this manner it is possible to provide a hand-held portable densitometer which is capable of (i) determining what type of target is being examined, (ii) selecting and storing the appropriate density measurements and, (iii) calculating and displaying percent trap and percent dot area when sufficient information has been measured and/or stored. Of course the densitometer displays all referenced density measurements to the pressman as well for use in controlling the printing process.

To the extent not already indicated, it will also be understood by those of ordinary skill in the art that any one of the specific embodiments and features of the invention herein described and illustrated may be further modified to incorporate features shown in other of the specific embodiments.

The invention in its broader aspects therefore is not limited to the specific embodiments herein shown and described but departures may be made therefrom within the scope of the accompanying claims without departing from the principles of the invention and without sacrificing its chief advantages.

What is claimed is:

1. A method for recognizing the type of printed target and controlling a multi-color printing process, comprising the steps of:

measuring the red, green, blue and visual optical densities of a selected target;

determining from said measured optical densities whether an unprinted substrate has been measured and, if an unprinted substrate has been measured, displaying that an unprinted substrate has been measured and repeating the above measuring step at a different target location;

where an unprinted substrate is not detected, determining from said measured optical densities whether a solid black target has been measured and, if a solid black target has been measured, displaying that a solid black target has been measured, storing the measured visual optical density as $S_V$ and repeating the above measuring step at a different target location;

where an unprinted substrate or black solid is not detected, determining from said measured optical densities and from the difference between the largest and smallest measured optical densities whether an overprint has been measured and, if an overprint has been measured, measuring the first down color red, green and blue optical densities, measuring the second down color red, green and blue optical densities, calculating from said optical densities of the overprint, the first down color and the second down color, the percent trap of the overprint; and displaying said percent trap, whereafter the above measuring step is repeated at a different target location;

where an unprinted substrate, a black solid or an overprint is not detected, determining from said measured optical densities whether a solid color target has been measured and, if a solid color target has been measured, storing the greatest measured optical density as the corresponding solid density and repeating the above measuring step at a different target location;

where a halftone is detected, that is, not an unprinted substrate, overprint or black or color solid, calculating percent dot area from the largest halftone optical density and the corresponding stored solid density, if available, whereupon the percent dot area is displayed;

controlling the printing process based upon the information generated in the preceding steps.

2. The method as in claim 1 wherein percent trap is calculated using the formula $$\frac{T - T_1}{T_2} \times 100$$

where:

$T_2$ = the largest measured optical density selected from the red, green or blue optical densities of the second down color, $T_1$ = the corresponding measured optical density of the first down color and $T$ = the corresponding measured optical density of the overprint.

3. The method according to claim 2 further comprising the steps of:

determining, when an overprint is detected, whether a red, green or blue overprint has been detected; and displaying the color overprint detected to the pressman.

4. The method according to claim 2 further comprising the step of storing, when an unprinted substrate is measured, the red, green, blue and visual unprinted substrate optical densities as $W_r$, $W_g$, $W_b$, $W_v$, respectively.

5. The method according to claim 4 wherein the percent dot area is calculated using the formula $$\frac{1 - 10^{-D_h/n}}{1 - 10^{-S/n}} \times 100$$

where:

$D_h$ = the largest measured halftone density, $S$ = the solid density corresponding to $D_h$ $n$ = Yule Nielsen factor.

6. The method according to claim 1 further comprising the following step performed immediately after said measuring step:

subtracting corresponding stored substrate optical densities from said measured optical densities to obtain referenced optical densities which are used in all subsequent calculation and display steps.

7. A method for recognizing the type of printed target and controlling a multi-color printing process comprising the steps of:

measuring the red, green, blue and visual optical densities of a selected target;

comparing said measured optical densities to a first stored constant K1 to determine whether an unprinted substrate has been measured and, if an unprinted substrate has been measured, displaying that an unprinted substrate has been measured and repeating the above measuring step at a different target location;

where an unprinted substrate is not detected, comparing said measured optical densities to a second stored constant K2 to determine whether a solid black target has been read and, if a solid black target has been read, storing the measured visual optical density as $S_V$, displaying that a solid black target has been read, and repeating the above measuring step at a different target location;

whether neither an unprinted substrate nor a solid black target is detected, comparing the measured red, green and blue optical densities to a third stored constant K3 and comparing the difference between the largest and smallest of the red, green and blue measured optical densities to a fourth stored constant K4 to determine whether an overprint has been measured and, if an overprint has been measured, performing an overprint check as follows;

comparing the measured green optical density to the measured red optical density and, where the green density is less than the red density, concluding that an overprint has been measured, where the measured green density is greater than or equal to the measured red density, comparing the measured blue optical density to the red density and, where the blue density is less than the red density, concluding that an overprint has been measured, where the measured blue optical density is greater than or equal to the red density, comparing the blue density to a fifth stored constant K5 such that, if the blue density is less than K5, it is concluded that a muddy solid magenta has been read, that a muddy solid magenta has been read is displayed, the measured green optical density is stored as $S_g$ and the above measuring step is repeated, whereas if the blue density is greater than or equal to K5 it is concluded that an overprint has been measured, and where it is concluded that an overprint has been measured, the following additional steps are performed to determine and display percent trap, (i) storing the measured red, green and blue optical densities as overprint values $T_r$, $T_g$ and $T_b$, respectively, (ii) measuring the red, green and blue optical densities of the first down color and storing these values as $T_{1r}$, $T_{1g}$ and $T_{1b}$, respectively, (iii) measuring the red, green and blue optical densities of the second down color and storing the greatest measured value as $T_2$, (iv) calculating percent trap using the equation $$\frac{T - T_1}{T_2} \times 100$$

where T and $T_1$ are the overprint and first down color density values corresponding to the filter color designated as $T_2$, and (v) displaying percent trap, whereupon the above measuring step is repeated on a different target location;

where none of an unprinted substrate, a solid black, a muddy magenta or overprint are detected, comparing the measured red, green and blue optical densities to a sixth stored constant K6 to determine whether a solid color target has been measured and, if a solid color target has been measured, storing the largest of the measured red, green or blue optical density as the corresponding solid density $S_r$, $S_g$, $S_b$ and repeating the above measuring step on a different target location;

where none of an unprinted substrate, a solid black, a muddy magenta, an overprint or a solid color are detected, comparing the difference between the largest and smallest measured red, green and blue optical densities to a seventh stored constant K7 such that, if the difference is less than K7 a black halftone is assumed and if the difference is greater than or equal to K7 a color halftone is assumed, whereupon percent dot area may be determined for the halftone using the equation $$\frac{1 - 10^{-D_h/n}}{1 - 10^{-S/n}} \times 100$$

where:
$D_h$ = the largest measured halftone density,
S = the solid density corresponding to $D_h$,
n = Yule-Nielsen factor,
the percent dot are being displayed;

controlling the printing process based upon the information generated and displayed in the foregoing steps.

8. The method according to claim 7 further comprising the step of storing, when an unprinted substrate is detected, the red, green, blue and visual unprinted substrate optical densities as $W_r$, $W_g$, $W_b$, $W_v$, respectively.

9. The method according to claim 7 further comprising the following step performed immediately after said measuring step:

subtracting corresponding stored substrate optical densities from said measured optical densities to obtain referenced optical densities which are used in all subsequent calculations and displays.

10. A densitometer system for recognizing the type of target in a multi-color printing process comprising:

measuring means for measuring the red, green, blue and visual optical densities of a selected target;

first comparison means for determining, from said measured optical densities, whether an unprinted substrate is detected and, if an unprinted substrate is detected, displaying than an unprinted substrate is detected, whereupon said measuring means measures a different target;

second comparison means for determining, where an unprinted substrate is not detected, whether a solid black has been measured and, if that a solid black has been measured, displaying that a solid black has been measured and storing the measured visual optical density as the corresponding solid visual density, whereupon said measuring means measures a different target;

third comparison means for determining from said measured optical densities, where neither an unprinted substrate nor a solid black is detected, whether an overprint has been measured, whereupon, (i) an overprint density value storage means stores the measured red, green and blue optical densities as $T_r$, $T_g$, $T_b$ respectively, (ii) an overprint check means determines whether an overprint has been measured and separately measures and stores the first down color red, green and blue optical densities and the second down color red, green and blue optical densities, (iii) a percent trap means determines percent trap from said measured optical densities of said overprint and said first and second down colors, and (iv) a percent trap display means displays the percent trap, whereafter said measuring means measures a different target;

fourth comparison means for determining, where an unprinted substrate, a black solid or an overprint is not detected, whether a solid color has been measured, whereupon the greatest of the measured red, green or blue optical densities is stored by a solid density value storage means as the corresponding solid color density; and percent dot area means for determining and displaying percent dot area where a halftone is detected, that is, where an unprinted substrate, a solid black, an overprint or a solid color target is not detected.

11. The densitometer system according to claim 10 wherein said percent dot area means, determines percent dot area using the formula $$\frac{1 - 10^{-D_h/n}}{1 - 10^{-S/n}} \times 100$$

where
$D_h$ = the largest measured halftone density,
S = the solid density corresponding to $D_h$, and
n = Yule Nielsen factor displays either the calculated percent dot area
or an error signal if no corresponding solid density value has been stored.

12. The system according to claim 10 wherein said overprint check means also determines whether a red, green or blue overprint has been detected and said percent trap display means also displays the color overprint detected.

13. A densitometer system for recognizing the type of target in a multi-color printing process comprising:

measuring means for measuring the red, green, blue and visual optical densities of a selected target;

first comparison means for comparing said measured optical densities to a first stored constant K1 to determine whether an unprinted substrate has been measured and, if an unprinted substrate has been measured, displaying that an unprinted substrate has been measured, whereupon said measuring means measures a different target;

second comparison means for comparing, where an unprinted substrate is not detected, said measured optical densities to a second stored constant value K2 to determine whether a solid black target has been read, whereupon the measured visual optical density is stored as the corresponding solid density $S_v$, that a solid black target has been read is displayed and said measuring means measures a different target;

third comparison means for comparing, where neither an unprinted substrate nor a solid black target is detected, the measured red, green and blue optical densities to a third stored constant K3 and for comparing the difference between the largest and smallest of the measured red, green and blue optical densities to a fourth stored constant K4 to determine whether an overprint has been measured, whereupon an overprint check means performs an overprint check by;

comparing the measured green density to the measured red density and, if the green density is less than the red density, concluding that an overprint has been measured, where the green density is greater than or equal to the red density, comparing the blue density to the red density, and where the blue density is less than the red density, concluding that an overprint has been measured, where the blue density is greater than or equal to the red density, comparing the blue density to a fifth stored constant K5 such that, if the blue density is less than K5 it is concluded that a muddy solid magenta has been read, that a muddy solid magenta has been read is displayed, the measured green optical density is stored as $S_g$ and said measuring means measures a different target, whereas if the blue density is greater than or equal to K5 it is concluded that an overprint has been measured, and where it is concluded that an overprint has been measured, said overprint check means, (i) stores the measured red, green and blue optical densities as overprint values $T_r$, $T_g$ and $T_b$, respectively, (ii) measures the red, green and blue optical densities of the first down color and stores these values as $T_{1r}$, $T_{1g}$ and $T_{1b}$, respectively, (iii) measures the red, green and blue optical densities of the second down color and stores the greatest measured value as $T_2$, (iv) calculates percent trap using the equation $$\frac{T - T_1}{T_2} \times 100$$

where T and $T_1$ are the overprint and first down color density values corresponding to the filter color of the density value designated $T_2$, (v) displays percent trap, whereupon said measuring means measures a different target portion;

fourth comparison means for comparing, where an unprinted substrate, a solid black, a muddy magenta or an overprint is not detected, the measured red, green and blue optical densities to a sixth stored constant K6 to determine whether a solid color target has been measured and, if a solid color target has been measured, storing the greatest measured optical density as the corresponding solid optical density, $S_r$, $S_g$ or $S_b$; and percent dot area means for comparing, where an unprinted substrate, a black solid, a muddy magenta, an overprint or a color solid is not detected, the difference between the largest and smallest of the measured red, green and blue optical densities to a seventh stored constant K7 such that, if the difference is less than K7 a black halftone is assumed and if the difference is greater than or equal to K7 a color halftone is assumed, whereupon said percent dot area means may determine percent dot area for the halftone using the equation $$\frac{1 - 10^{-D_h/n}}{1 - 10^{-S/n}} \times 100$$

where:
$D_h$ = the largest measured halftone density,
S = the solid density corresponding to $D_h$,
n = Yule-Nielsen factor, and
said percent dot area means displaying either the calculated percent dot area of an error signal where no value has been stored for the corresponding solid density.

14. The system according to claim 13 further comprising substrate density storage means for storing the red, green blue and visual optical densities of an unprinted substrate.

15. The system according to claim 13 wherein said measuring means subtracts corresponding stored substrate optical density values from said measured optical density values to obtain referenced densities used in all calculations and displays.

16. The system according to claim 13 wherein said overprint check means also determines whether a red, green or blue overprint has been detected and displays the color overprint as well as percent trap to the pressman.

17. A densitometer system for recognizing the type of target in a multi-color printing process comprising:
measuring means for measuring the red, green, blue and visual optical densities of a selected target;
comparison means for determining from said measured optical densities whether an overprint has been measured, whereupon,
(i) an overprint density value storage means stores the measured red, green and blue optical densities at $T_r$, $T_g$, $T_b$, respectively,
(ii) an overprint check means determines whether an overprint has been measured and separately measures and stores the first down color red, green and blue optical densities and the second down color red, green and blue optical densities,
(iii) a percent trap means determines percent trap from said measured optical densities of said overprint and said first and second down colors, and
(iv) a percent trap display means displays the percent trap.

18. A densitometer system for recognizing the type of target in a multi-color printing process comprising:
measuring means for measuring the red, green, blue and visual optical densities of a selected target;
first comparison means for determining, from said measured optical densities, whether an unprinted substrate is detected and, if an unprinted substrate is detected, displaying that an unprinted substrate is detected, whereupon said measuring means measures a different target;
second comparison means for determining, where an unprinted substrate is not detected, whether a solid black has been measured and, if a solid black has been measured, displaying that a solid black has been measured and storing the measured visual optical density as the corresponding solid visual density, whereupon said measuring means measures a different target;
third comparison means for determining, where neither an unprinted substrate nor a black solid are detected, whether a solid color target has been measured, whereupon the greatest of the measured red, green or blue optical densities is stored by a solid density value storage means as the corresponding solid color density and said measuring means measures a different target; and
percent dot area means for determining whether a halftone is detected, whereupon said percent dot area means determines and displays percent dot area based on said measured optical density and said stored solid density values.

* * * * *